US007884190B2

(12) United States Patent
Cohen et al.

(10) Patent No.: US 7,884,190 B2
(45) Date of Patent: Feb. 8, 2011

(54) RECOMBINANT DIMERIC AND HETERODIMERIC PROTEINS COMPRISING AMINO ACIDS 193 TO 252 OF THE β CHAIN OF THE HUMAN C4BP PROTEIN

(75) Inventors: Jacques Henri Max Cohen, Reims (FR); Stéphane Oudin, Strasbourg (FR); Xavier Dervillez, Francfort sur le Main (DE); Annelise Gimenez, Saint Memmie (FR); Béatrice Donvito, Reims (FR); Marcelle Tonye-Libyh, Reims (FR)

(73) Assignee: Universite de Reims Champagne-Ardenne, Reims (FR)

( * ) Notice: Subject to any disclaimer, the term of this patent is extended or adjusted under 35 U.S.C. 154(b) by 804 days.

(21) Appl. No.: 11/583,164

(22) Filed: Oct. 19, 2006

(65) Prior Publication Data

US 2007/0190615 A1    Aug. 16, 2007

Related U.S. Application Data

(63) Continuation of application No. PCT/FR2005/001007, filed on Apr. 22, 2005.

(30) Foreign Application Priority Data

Apr. 22, 2004    (FR) .................................. 04 04295

(51) Int. Cl.
C07K 14/00 (2006.01)
C12P 21/06 (2006.01)
C12N 9/00 (2006.01)
C12N 1/20 (2006.01)
C12N 15/00 (2006.01)
C07H 21/04 (2006.01)

(52) U.S. Cl. ..................... 530/350; 435/69.1; 435/183; 435/252.3; 435/320.1; 536/23.2

(58) Field of Classification Search ....................... None
See application file for complete search history.

(56) References Cited

FOREIGN PATENT DOCUMENTS

FR    2 736 916    1/1997
WO    WO 9704109    * 2/1997

OTHER PUBLICATIONS

Chica et al. Curr Opin Biotechnol. Aug, 2005;16(4):378-84.*
Sen et al. Appl Biochem Biotechnol. Dec. 2007;143(3):212-23.*
Oudin S et al: "A soluble recombinant multimeric anti-Rh(D) single-chain Fv/CR1 molecule restores the immune complex binding ability of CR1-deficient erythrocytes" Journal of Immunology, The Williams and Wilkins Co. Baltimore, US, vol. 164, No. 3, Feb. 1, 2000, pp. 1505-1513.
Libyh M T et al: "A recombinant human scFv anti-Rh(D) antibody with multiple valences using a C-terminal fragment of C4-binding protein" Blood, W.B. Saunders Company, Orlando, FL, US, vol. 90, No. 10, Nov. 15, 1997, pp. 3978-3983.
Blom A M et al: "The C4b-binding protein-protein S interaction is hydrophobic in nature" Biochimica Et Biophysica Acta. Protein Structure and Molecular Enzymology, Elsevier, Amsterdam, NL, vol. 1388, No. 1, Oct. 14, 1998, pp. 181-189.
Webb J.H., et al: "Role of CCP2 of the C4b-binding protein beta-chain in protein S binding evaluated by mutagenesis and monoclonal antibodies" Eur. J. Biochem., vol. 270, 2003, pp. 93-100.

* cited by examiner

Primary Examiner—Christian L Fronda
(74) Attorney, Agent, or Firm—Young & Thompson

(57) ABSTRACT

A method for preparing recombinant dimeric proteins using a nucleic acid coding for the C-terminal fragment of the C4BP protein β chain including amino acid residues 193 to 252 or a functional variant of the fragment, wherein the fragment enables covalent bonding of the heterologous polypeptides to which it is fused. Dimeric proteins obtained by means of the method and cells for carrying out the method are also described.

15 Claims, 4 Drawing Sheets

RECOMBINANT DIMERIC AND HETERODIMERIC PROTEINS COMPRISING AMINO ACIDS 193 TO 252 OF THE β CHAIN OF THE HUMAN C4BP PROTEIN

The invention relates to a method for obtaining recombinant dimeric proteins, using a nucleic acid coding for the C-terminal fragment of the β chain of the C4BP protein comprising amino acid residues 193 to 252 or a functional variant of that fragment, said fragment allowing covalent association of polypeptides heterologous to that to which it is fused. The invention also relates to dimeric proteins which may be obtained by the method and to cells for implementing the method.

The possibility of producing a protein of interest in a heterologous expression system constitutes a major application of molecular biology. In particular, the production of proteins of interest in heterologous systems means that high production yields can be produced at low costs and the risks of contamination by undesirable elements, for example viruses or prions are limited with respect to with methods for purifying native proteins.

Examples of recombinant biomolecules of interest in biotechnology which may be cited are antigens, antibodies or fragments thereof, in particular their fragments comprising all or part of the variable chains, enzymes, hormones, cytokines or growth factors for the production of vaccines, diagnostic kits or molecules with therapeutic activity.

In order to have a desired biological activity or to exhibit optimum biological activity, many biomolecules must be assembled into the form of a dimer. To produce them, it is thus necessary to ensure that the dimerisation step is carried out correctly. Depending on the nature of the monomers, assembly into a dimer occurs spontaneously following synthesis of the monomers, in general in the endoplasmic reticulum, before their secretion into the extracellular medium. However, in some cases, in particular when the dimers are not properly assembled or not assembled, it is necessary to resort to a supplemental covalent coupling step for the monomers. Coupling methods are also required to produce particular heterodimers.

The prior art discloses-coupling methods using a chemical bridging agent to obtain a conjugate. Coupling is then obtained by maleimide, succinimide, peptide, disulfide and thioether type bonds. In particular, reference can be made to the work "Bioconjugate techniques" by Greg T HERMAN-SON (Academic Press, 1996).

An example of one particular method consists of adding, to one end of a recombinant peptide, a heterologous peptide termed a "linker" peptide which can easily be used for disulfide, amine or acid bonds. Another approach consists of chemically coupling a biotinyl group which can then couple any substance bound to streptavidin.

A general review of such coupling methods can, for example, be seen in: Methods of Immunological Analysis, Volume 2, Rene Masseyeff, Winfried Albert, Norman A. Staines, VCH. December 1992; Handbook of experimental immunology, Volume 1, 2nd Edition, Ed. D. M. Weir, Blackwell Scientific Publications, Oxford.

Existing methods necessitate a chemical reaction step which is supplemental to the synthesis step proper for the monomers, and are often ill suited to large scale production of dimeric proteins. Further, for certain in vivo applications, it may be necessary to avoid the use of potentially immunogenic bridging agents.

Other methods have been proposed for the production of dimeric proteins, consisting of producing a fusion polypeptide, the fusion polypeptide being constituted by a polypeptide of interest and a functional domain allowing dimerization.

The dimerization domains selected are, for example, domains of CL and CHI antibodies, calmodulin or the corresponding calmodulin linker peptide or streptavidin (Müller et al, FEBS Lett, 1998, 422: 259-264, Neri et al, Biotechnology, 1995, 13: 373-377).

Finally, the most frequently used method consists of expressing a single nucleic acid coding for two polypeptides which are linked together via a peptide linker. The peptide linker, however, has the disadvantage of being potentially immunogenic and thus may not be satisfactory in all of the applications envisaged for a dimeric protein, in particular a protein intended to be administered to humans or animals.

As a result, there exists a need to identify a simple method for producing recombinant dimeric proteins of interest which assemble) spontaneously without the need for a supplemental polymerization step.

There is also a need to identify a method that can produce recombinant dimeric proteins of interest the association of which does not necessitate the use of potentially immunogenic molecules.

The present invention aims to overcome, at least in part, the disadvantages of the methods described above for the production of recombinant dimeric proteins.

The C4BP protein is involved in coagulation and the complement system. The major form of C4BP is composed of 7 identical 75 kD α chains and one 45 kD β chain. The α and β chains respectively contain 8 and 3 SCR (short consensus repeat) domains, those motifs being found in many complement-regulating proteins and constituted by 50-70 amino acids organized into β sheets.

The role of the α chain in polymerizing the C4BP protein has been studied by Kask et al (Biochemistry 2002, 41, 9349-9357). Those authors have in particular shown that the C-terminal portion of the α chain, in particular its α helical structure and the presence of two cysteines, is necessary for polymerization of the C4BP protein when the α chain is expressed in a heterologous system.

Further, the production of polymers constituted by subunits of antibody fragment or of complement receptor CR1 fused to the C-terminal portion of the α chain of C4BP has also been described (Libyh et al, Blood, 1997, 90: 3978-3983; Oudin et al, J Immunol 2000, 164, 1505-1513).

European patent application EP-A-2 227 030 also describes the production of heteromultimeric recombinant proteins by using C-terminal fragments of the α and β chains of the C4BP protein in fusion with polypeptides of interest.

To the Applicant's knowledge, the use of the β chain of the C4BP protein, independently of its use in association with the α chain of the C4BP protein, has never been described for the production of multimeric proteins, in particular for the production of dimeric proteins.

The inventors have now, surprisingly, established that expression in a heterologous system of a nucleic acid coding, in fusion, for the C-terminal fragment of the β chain of the C4BP protein and a polypeptide of interest, allows recombinant dimeric proteins the monomers of which are covalently bound.

Hence, the invention concerns a method for producing a recombinant dimeric protein comprising:

a) Transfecting host cells with a vector allowing expression of a nucleotide sequence coding for a fusion polypeptide, said fusion polypeptide comprising at least the fragment constituted by amino acids in positions 193 to 252 of the β chain of the human C4BP protein or a functional variant of said fragment by deletion, addition or substitution of one or more amino acids, conserving the capacity to form an at least dimeric protein, said fusion polypeptide further comprising a polypeptide which is heterologous to said β chain;

b) culturing transfected cells under conditions which are suitable for expressing the nucleotide sequence coding for the fusion polypeptide and the covalent association of two fusion polypeptides in vivo to form a dimeric protein;

c) recovering the dimeric proteins formed.

To obtain a dimeric protein which is not hexa- or heptameric, the heterologous system preferably does not contain any nucleic acid allowing expression or over-expression of the C-terminal fragment of the α chain of the C4BP protein, involved in polymerizing C4BP.

Within the context of the invention, the term "polypeptide heterologous to the β chain" means any polypeptide characterized in that the sequence of that polypeptide is not naturally associated with the fragment of the β chain to which it is fused. Preferably, it is a polypeptide which does not alone have the capacity to associate covalently with another polypeptide to form a homodimer or a heterodimer.

Examples of heterologous polypeptides which may be cited are enzymes, enzymatic activity regulation factors, receptor ligands, haptens, antigens, antibodies, antibody fragments or receptors, in particular monochain receptors or proteic drug acceptors.

Clearly, the skilled person will select the sequence of a heterologous polypeptide as a function of the desired application. The sequences of polypeptides may, for example, be selected from the active principles of drugs, including immunotoxins, antioxidants, antibiotics, growth factors, intracellular hormones, cytokines, toxins, neuromediators, antimicrobial agents, in particular antivirals, antibacterials and antiparasitics, or antineoplastics or any other therapeutic agent or prophylactic agent of interest.

In particular, the polypeptide sequences are selected from immunoglobulins and antibody fragments, in particular fragments corresponding to variable domains or to immunologically active portions of those domains, such as scFvs (single chain fragment variable), dimeric enzymes such as fumarylacetoacetate hydrolase, or dimeric receptors such as the receptor for C3Bi (CD11+CD18).

The polypeptide sequence of the β chain of the human C4BP protein has been described by Hillarp and Dahlbaick (1990, PNAS vol 87, pp 1183-1187), as well as the cDNA sequence coding therefore.

A sequence for the β chain of the C4BP protein and its cDNA has also been described in the NCBI database, accession number NM_000716, the protein numbering of which is used herein.

The fragment corresponding to positions 193 to 252 is identified by reference to this sequence and may, for example, be obtained by PCR amplification from a human cDNA library choosing primers which specifically hybridize to the corresponding ends of the sequence coding for the desired fragment of the β chain. It may alternatively be obtained by any appropriate method which is known to the skilled person.

For simplification here, the term "193 to 252 fragment" or "193 to 252 fragment of the β chain", unless otherwise indicated, means the fragment constituted by the consecutive concatenation of amino acids in positions 193 to 252 of the β chain of the human C4BP protein.

In a preferred implementation, the 193 to 252 fragment of the β chain of the human C4BP protein has the following polypeptide sequence:

LIQEAPKPECEKALLAFQESKNLCEAMENFMQQLKESGMTMEELKYSLEL
KKAELKAKLL

A nucleic acid sequence corresponding to this polypeptide sequence has also been described by Hillarp and Dahlback (1990, PNAS, vol 87, pp 1183-1187).

To produce the recombinant dimeric proteins of the invention, the skilled person may also use a sequence coding for a functional variant of the 193 to 252 fragment, conserving the capacity to form at least one dimer, for example a homodimer or a heterodimer, a trimer, a tetramer or any multimer containing a different number of fusion polypeptides.

Within the context of the invention, the term "functional variant of the fragment 193 to 252" means a polypeptide sequence modified with respect to the sequence of fragment 193 to 252 of the β chain by deletion, substitution or addition of one or more amino acids, said modified sequence retaining, however, the capacity to form at least dimeric proteins using the method of the invention. More precisely, the production of dimeric proteins using a sequence coding for a functional variant of the fragment 193 to 252 must be at least 80% equal to that obtained with a native sequence coding for the fragment 193 to 252, preferably at least 90%, in an identical expression system. Preferably, the variant is such that more than 80% of the fusion polypeptides which it contains are produced in the form of dimers in a eukaryotic expression system in accordance with the invention.

In a first particular implementation, a functional variant corresponds in particular to a fragment of the β chain containing the 193 to 252 fragment and also containing a sequence adjacent to the β chain upstream of that fragment including, for example, the last SCR sequence (residues 136-192) and/or 4 or 5 [GS] amino acids. Sequences coding for longer fragments of the β chain, or even the whole β chain, may also be used. For certain applications, it is preferable to avoid using a sequence coding for a β chain which is capable of binding the S protein participating in coagulation. If the selected sequence codes for a fragment containing the two first SCR motifs of the β chain, these will preferably by versions mutated by addition, deletion or substitution of amino acids to cut out with the possibility of interaction with the S protein. SCR motifs and/or [GS] domains may be added with the aim of modifying, for example increasing, the flexibility of the fusion polypeptide obtained or to allow the fusion polypeptides or the heterologous polypeptides to adopt a suitable conformation to form multimers, particularly dimers, which are appropriate to its biological activity (binding, catalyzing the enzyme reaction, interaction with drugs).

In a particular implementation, a sequence coding for a variant of the 193 to 252 fragment of the β chain is a sequence the corresponding nucleic acid of which is capable of hybridizing under stringent conditions with the sequence coding for the 193 to 252 fragment, as described by Hillarp and Dahlback (1990, PNAS, Vol. 87, pp 1183-1187).

The term "stringent conditions" means conditions which allow specific hybridization of two single strand DNA sequences at about 65° C., for example, in a solution of 6×SSC, 0.5% SDS, 5×Denhardt's solution and 100 μg of non specific DNA or any other solution with an equivalent ionic strength and after washing at 65° C., for example in a solution of at most 0.2×SSC and 0.1% SDS or any other solution with an equivalent ionic strength.

Preferably, the nucleotide sequence (polynucleotide) coding for a functional variant of said 193 to 252 fragment and hybridizing under stringent conditions with the sequence coding for said fragment has, in the portion which hybridizations, a length of at least 50%, preferably at least 80%, of the length of the sequence coding for the 193 to 252 fragment. In a particular implementation, the nucleotide sequence (polynucleotide) coding for a functional variant of said 193 to 252 fragment and hybridizing under stringent conditions with the sequence coding for said fragment has, in the portion which hybridizations, substantially the same length as the sequence coding for said 193 to 252 fragment.

In a further implementation, a functional variant is a modified sequence of the 193 to 252 fragment one or more amino acids of which, not essential to the dimerization function, have been removed or substituted and/or one or more amino acids essential to dimerization have been replaced by amino acids with equivalent functional groups (conservative substitution). It is particularly recommended that the two cysteines, located at positions 201 and 215, and the peptide structure around these cysteines be conserved to allow the formation of disulfide bridges which are necessary for dimerization, for example by conservation of at least 3 amino acids upstream and downstream of each cysteine. In particular, a functional variant may also be obtained by inserting a heterologous sequence of the β chain, and in particular domains of the β chain of C4BP, between the cysteines responsible for dimerization or, in contrast, by doing away with certain amino acids present between those same cysteines. Alternatively, a functional variant may be produced by point modification of certain amino acids, in particular substitution of a cysteine responsible for dimerization by a neutral amino acid as regards implication in the dimerization process (for example the amino acids A, V, F, P, M, I, L and W) and at the same time substituting another amino acid by a cysteine to conserve the capacity to form intracatenary and/or intercatenary disulfide bridges between the cysteines. These modifications thus result in a variation in the distance between the various cysteines involved in the multimerization process, in particular dimerization.

The modifications to the β chain of the C4BP protein may in particular be determined to modify, in particular improve, accessibility of the heterologous polypeptide in the fusion polypeptide, for example by modifying the flexibility of the fusion polypeptide.

Preferably, less than 50% of the amino acids of the 193 to 252 fragment are done away with or replaced, preferably less than 25% or even less than 10% (for example 5 amino acids or fewer) or less than 5% (1 or 2 amino acids).

The sequences coding for the C-terminal fragment of the β chain and coding for the polypeptide of interest are fused and cloned into a suitable expression vector. Preferably, the fusion polypeptide coded for by the nucleotide sequence contains in its N-terminal portion, the heterologous polypeptide and in its C-terminal portion, the fragment of the β chain of the C4BP protein.

The expression vector is selected as a function of the host cell into which the construct is introduced. Preferably, the expression vector is selected from vectors that allow expression in eukaryotic cells, especially from chromosomal vectors or episomal vectors or virus derivatives, in particular vectors derived from plasmids, yeast chromosomes, or from viruses such as baculovirus, papovirus or SV40, retroviruses or combinations thereof, in particular phagemids and cosmids. Preferably, it is a vector allowing the expression of baculovirus, capable of infecting insect cells.

If necessary, the sequence coding for the fusion polypeptide also comprises, preferably in its 5' portion, a sequence coding for a signal peptide for the secretion of fusion polypeptide. Conventionally, the sequence of a signal peptide is a sequence of 15 to 20 amino acids, rich in hydrophobic amino acids (Phe, Leu, Ile, Met and Val). Examples of signal peptides which may in particular be cited are the signal peptide gp67 as used in the expression vector selected in the experimental section.

The vector comprises all of the sequences necessary for the expression of the sequence coding for the fusion polypeptide. In particular, it comprises a suitable promoter, selected as a function of the cell into which the construct is to be introduced.

An example of an expression vector for baculovirus is described in the experimental section.

Within the context of the invention, the term "host cell" means a cell capable of expressing a gene carried by a nucleic acid which is heterologous to the cell and which has been introduced into the genome of that cell by a transfection method. Preferably, a host cell is a eukaryotic cell. A eukaryotic host cell is in particular selected from yeast cells such as *S cerevisiae*, filamentous fungus cells such as *Aspergillus* sp, insect cells such as the S2 cells of Drosophila or sf9 of Spodoptera, mammalian cells and plant cells.

Mammalian cells which may in particular be cited are mammalian cell lines such as CHO, COS, HeLa, C127, 3T3, HepG2 or L(TK-) cells.

In a preferred implementation, said host cells are selected from eukaryotic cell lines, preferably Sf9 insect cells.

Any transfection method known to the skilled person for the production of cells expressing a heterologous nucleic acid may be used to carry out step a) of the method. Transfection methods are, for example, described in Sambrook et al, 2001, "Molecular Cloning: A Laboratory Manual", $3^{rd}$ edition, Cold Spring Harbor Laboratory Press, Cold Spring Harbor, N.Y.

In a particular implementation of the method of the invention, the host cell allows co-expression of two fusion polypeptides, a first fusion polypeptide A constituted by fusion of a 193 to 252 fragment or a functional variant of that fragment with a polypeptide of interest A'; and a second fusion polypeptide B constituted by fusion of a 193 to 252 fragment or a functional variant of that fragment with a polypeptide of interest B'. In this particular implementation, co-expression of the two fusion polypeptides can also allow the production of homodimers A-A and B-B and the production of heterodimers A-B.

The polypeptides of interest A' and B' are selected, independently of each other, from the group constituted by enzymes, enzymatic activity regulating factors, receptor ligands, haptens, antigens, antibodies, antibody fragments, drugs, receptors, in particular monochain receptors or proteic drug acceptors.

The expression "selected independently of each other" means that the two polypeptides of interest A' and B' (or heterologous polypeptides) may be of different natures, i.e. one is an enzyme and the other is a receptor, for example, or vice versa, i.e. two ligands, two antibodies or monochain receptors. When the nature of the heterologous polypeptides is identical, then the two polypeptides may still be different, for example in their protein composition or in their post translational modifications; thus, the production method can also allow the production of heterodimers in which the first and second heterologous polypeptides of these heterodimers each comprise an antibody site which is different from the other polypeptide, a ligand which differs from that of the other polypeptide or a monochain receptor which differs from that of the other polypeptide.

The term "different" when referring to the examples of heterologous polypeptides means a protein sequence the primary sequence of which (amino acid sequence) of one of the heterologous polypeptides is different by at least one amino acid from the primary sequence of the other polypeptide. As an example, the primary sequences may be different for all of the amino acids while the proteins are of the same nature, for example two enzymes, two antigens or two haptens. Alternatively, the term "different" also covers heterologous polypeptides having the same primary sequence but having different post-translational modifications, for example in terms of acetylation, amidation, biotinylation, carboxylation, hydroxylation, methylation, phosphorylation or sulfatation, or by adding lipids (isoprenylation, palmitoylation and myristoylation), glucides (glycosylation) or polypeptides (ubiquitination).

The expression "antibody site" means protein sequences necessary for recognition of a given antigen, in particular variable domains (of heavy and/or light chains) of an immunoglobulin.

The term "protein drug acceptor" means any amino acid, peptide chain (at least two consecutive amino acids) or ensemble of amino acids (at least two non consecutive amino acids) interacting with a drug.

Thus, the invention also pertains to a method for producing heterodimers, said method comprising:
  a. transfecting host cells with one or more vectors to allow the expression of one or more nucleotide sequences coding for:
    i. a first fusion polypeptide, said fusion polypeptide comprising the 193 to 252 fragment of the β chain of the Human C4BP protein or a functional variant of said fragment and a first polypeptide heterologous to said β chain; and
    ii. a second fusion polypeptide, said fusion polypeptide comprising at least the 193 to 252 fragment of the D chain of the human C4BP protein or a functional variant of said fragment, and a second polypeptide heterologous to said β chain the sequence of which is different from that of the first heterologous polypeptide;
  b. culturing transfected cells under conditions appropriate for expressing the nucleotide sequence or sequences coding for the first and second fusion polypeptides and association of two fusion polypeptides in vivo to form a heterodimeric protein;
  c. recovering the heterodimeric proteins formed.

The invention also pertains to a recombinant dimeric or heterodimeric protein which may be obtained by one of the production methods described above.

The invention particularly pertains to a recombinant dimeric protein, characterized in that it is constituted by two fusion polypeptides, each fusion polypeptide comprising at least the 193 to 252 fragment of the β chain of the human C4BP protein or a functional variant of said fragment and a polypeptide heterologous to said β chain.

In a particular implementation, the recombinant dimeric protein of the invention is characterized in that said fusion polypeptides are associated by covalent binding between two cysteines of the fragment of the β chain of the C4BP protein.

Preferably, each monomer of the dimeric protein comprises the fragment of the β chain of the C4BP protein fused to the C-terminal end of a polypeptide heterologous to said β chain.

In a particular implementation, the heterologous polypeptide is selected from the group constituted by enzymes, enzymatic activity regulating factors, receptor ligands, haptens, antigens, antibodies, antibody fragments, drugs, receptors, especially monochain receptors or proteic drug acceptors. As an example, the antibody fragment comprises all or part of the variable regions of an antibody which is functional for antigen-antibody binding.

The invention also pertains to a recombinant heterodimeric protein, characterized in that it is constituted by a first and a second fusion polypeptide, each fusion polypeptide comprising at least one fragment constituted by amino acids in positions 193 to 252 of the β chain of the human C4BP protein or a functional variant of said fragment by deletion, addition or substitution of one or more amino acids conserving the capacity to form a protein which is at least dimeric, said first fusion polypeptide further comprising a polypeptide heterologous to said β chain, and the second fusion polypeptide comprising a second polypeptide heterologous to said β chain which differs from the first heterologous polypeptide.

In a particular implementation, the fragment of the β chain of the human C4BP protein, comprising at least the amino acids in positions 193 to 252, of the first and second fusion polypeptide or a functional variant of said fragment, are respectively fused to the C-terminal end of the first and second heterologous polypeptides.

The first and second heterologous polypeptides are selected, independently of each other, from the group constituted by enzymes, enzymatic activity regulating factors, receptor ligands, haptens, antigens, antibodies, antibody fragments, drugs and receptors, especially monochain receptors or proteic drug acceptors.

Hence, the heterodimers are characterized in that the first and second heterologous polypeptides are different ligands, different antibody sites or different monochain receptors.

In a preferred implementation, the heterodimeric protein comprises a first heterologous polypeptide which is an antibody and a second heterologous polypeptide which is a drug. In a further preferred implementation, the heterodimeric protein comprises a first heterologous polypeptide which is an antibody and a second heterologous polypeptide which is a proteic drug acceptor.

In a particular implementation, the recombinant heterodimeric protein of the invention is characterized in that said fusion polypeptides are associated by covalent bonding between two cysteines of the fragment of the β chain of the C4BP protein.

The invention also concerns a recombinant eukaryotic cell allowing synthesis of a dimeric or heterodimeric cell as defined above, and characterized in that it is capable of being obtained by carrying out step a) of the production method defined above. In a particular implementation, the recombinant eukaryotic cell of the invention is an insect cell, preferably a Sf9 cell line.

The invention also pertains to the use, in a method for producing a recombinant dimeric protein, of a nucleic acid coding for a fusion polypeptide, said fusion polypeptide comprising at least the 193 to 252 fragment of the β chain of the C4BP protein or a functional variant of said fragment and a polypeptide heterologous to said β chain.

Finally, the invention concerns the use, in a method for producing a recombinant heterodimeric protein, of two nucleic acids:
  a) a first nucleic acid coding for a first fusion polypeptide, said first fusion polypeptide comprising at least the fragment constituted by amino acids in positions 193 to 252 of the β chain of the human C4BP protein or a functional variant of the fragment by addition, deletion or substitution of one or more amino acids, conserving the capacity to form a heterodimeric protein, said first fusion polypeptide further comprising a first polypeptide heterologous to said β chain; and b) a second nucleic acid coding for a second fusion polypeptide, said second fusion polypeptide comprising at least the fragment constituted by amino acids in positions 193 to 252 of the β chain of the human C4BP protein or a functional variant of the fragment by addition, deletion or substitution of one or more amino acids, conserving the capacity to form a heterodimeric protein, said second fusion polypeptide further comprising a second polypeptide heterologous to said β chain the sequence of which differs from that of the first heterologous polypeptide.

The C4BP protein used to carry out the invention is advantageously the human C4BP protein.

The following examples illustrate certain preferred implementations of the method of the invention and facilitate comprehension of its implementation without in any way limiting the scope of the invention.

Track 1: culture supernatant from st9 cells infected with virus containing nucleic acid coding for anti GPA scFv fused with the C-terminal fragment of the β chain of the C4BP protein. Production of monomers and scFv/C4BPβdimers (in the majority);

Track 2: culture supernatant from sf9 cells infected with virus containing nucleic acid coding for anti GPA scFv fused with the C-terminal fragment of the α chain of the C4BP protein. Production of scFv/C4BPα heptamers;

Track 3: culture supernatant from sf9 cells infected with virus containing nucleic acid coding for a non-related recombinant protein. Negative control.

FIG. 3 shows the results of an agglutination test.

Column 1: anti-glycophorin A antibody, negative control;

Column 2: sf9 supernatant cells infected by recombinant virus (non related protein). Negative control;

Column 3: sf9 supernatant cells infected by recombinant scFv antiGPA/C4BPβ virus; agglutination of erythrocytes;

FIG. 4 is an auto radiogram of a gel of supernatant proteins after immunoprecipitation using an anti-CR1 J3D3 antibody. Track A shows electrophoresis under non-reducing conditions and track B shows electrophoresis under reducing conditions.

EXAMPLES

Production of a Recombinant Anti-GPA Dimeric Protein in sf9 Insect Cells

1) Preparation of Plasmid Allowing Expression of a Fusion Polypeptide.

A sequence coding for a fusion polypeptide constituted by an anti-GPA antibody recognition site (R18) (scFv) and a C-terminal fragment of the β chain (residues 137 to 252 of the β chain) was introduced into the (pAcgp67) baculovirus expression vector (Pharmingen, San Diego, USA; Stewart L M D, Hirst M, Nature 1991; 352: 85-88). FIG. 1 is a diagram of the plasmid obtained.

2) Transfection of sf9 Insect Cells.

The plasmid was co-transfected with linearized Baculogold DNA (Becton Dickinson, Le Pnt de Claix, France) in sf9 insect cells to obtain recombinant viruses.

3) Production of Dimeric Anti-GPA/C4BPβ scFv Proteins in sf9 Insect Cells.

Insect cells ($6\times10^6$ sf9 cells) were infected with recombinant virus ($6\times10^7$ viruses) in 10 ml of culture medium and incubated for 5 days at 27° C. using the conventional method described, for example, in the instruction manual entitled "Baculovirus expression system", May 99, Pharmingen, San Diego, USA and in the "Guide to baculovirus expression vector systems and insect cell culture techniques", Invitrogen, Cergy Pontoise, France. The culture supernatants were then concentrated 15 times on a YM-20 centricon (Millipore, St Quentin en Yvelines, France) then underwent SDS-PAGE gel electrophoresis with a 4-15% Tris-HCl gradient (BioRad, Marnes la Coquette, France) under native conditions. The Western blot was revealed by an anti-scFv antibody. The results are shown in FIG. 2. The results show that the majority of polypeptides containing the scFv fragment in fusion with the C-terminal fragment of the β chain (track 1) migrated in the form of dimeric proteins with a molecular weight of about 85 kDa. The polypeptides containing the scFv fragment in fusion with the C-terminal fragment of the α chain (track 2) migrated in the form of heptameric proteins with a molecular weight of more than 200 kDa.

4) Estimation of Concentration of scFv/C4BPβ Dimeric Proteins.

The supernatants were recovered 4 days (D4) and 6 days (D6) after infection. Assay of the concentrated supernatant and media was carried out using a spectrophotometer at 280 nm.

The proteins underwent polyacrylamide gel electrophoresis, denaturing with SDS (acrylamide 4-15%, Tris HCl) then the gel was stained with Coomassie blue. A measurement was then carried out on the gel to estimate the percentage of the quantity of proteins contained in each band with respect to the total protein quantity. The total protein concentration obtained was as follows:

D4, 0.65 g/l of scFvβ proteins;

D6, 0.63 g/l of scFvβ proteins.

The percentage of the peak corresponding to the band of interest was estimated to be 5.7% of the total quantity on D4, and 7.3% of the total quantity on D6, i.e. 47 mg/litre of dimeric proteins of interest were produced.

Compared to the number of cells, on D6, the yield obtained was about 76 μg of dimeric proteins/$10^6$ cells.

The scFv antiglycophorin A model shows that it is possible to produce recombinant dimeric proteins in insect cells, and to obtain their secretion in a single molecular form in a concentration which is of practical interest.

5. Functional Test for scFv/C4BPβ Protein: Hemagglutination

In order to verify that the dimers produced were functional, we checked that the proteins produced were capable of agglutinating erythrocytes and thus of recognizing glycophorin A.

To this end, red blood cells were washed three times in PBS. The culture supernatants were brought into contact with erythrocytes incubated for 45 minutes at 37° C. then placed on a DiaMed-ID NaCl Enzyme test and cold agglutinins column (DiaMed, Paris) and centrifuged.

The results presented in FIG. 3 show that the proteins produced are capable of agglutinating erythrocytes and are thus functional (column 3).

6. Production of a CR1/C4BPβ Dimeric Protein

CR1 (complementary receptor 1) is a transmembrane glycoprotein of erythrocytes which is involved in the capture and elimination of immune complexes. The density of CR1 is reduced in diseases such as AIDS or disseminated Lupus erythematosus.

Figure 1:
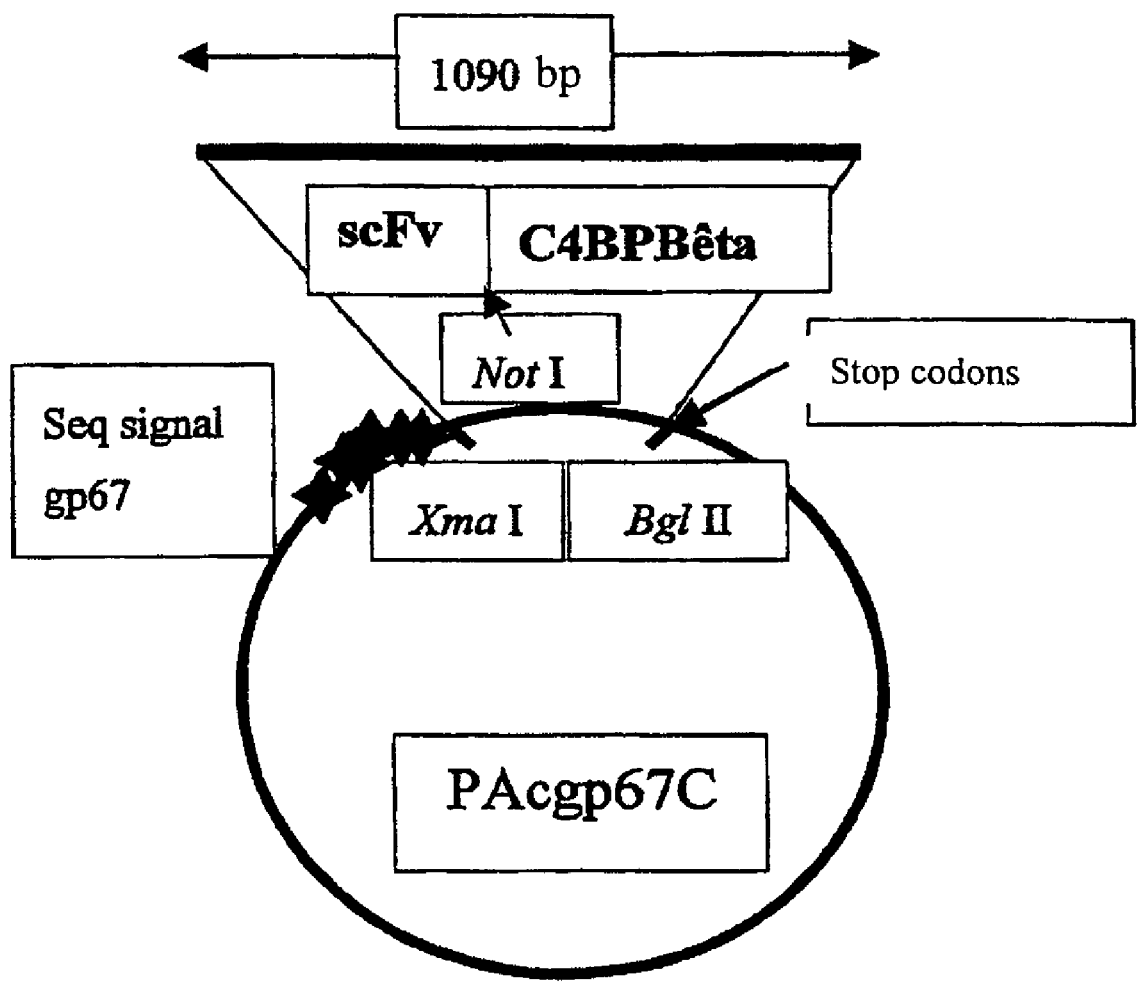
FIG. 1 is a diagram of the plasmid PAcgp76c into which the nucleic acid coding for the fusion polypeptide constituted by the GPA (glycophorin A) recognition site (scFv) and a C-terminal fragment of the β chain of the C4BP protein (C4BPbeta) has been introduced.
Figure 2:
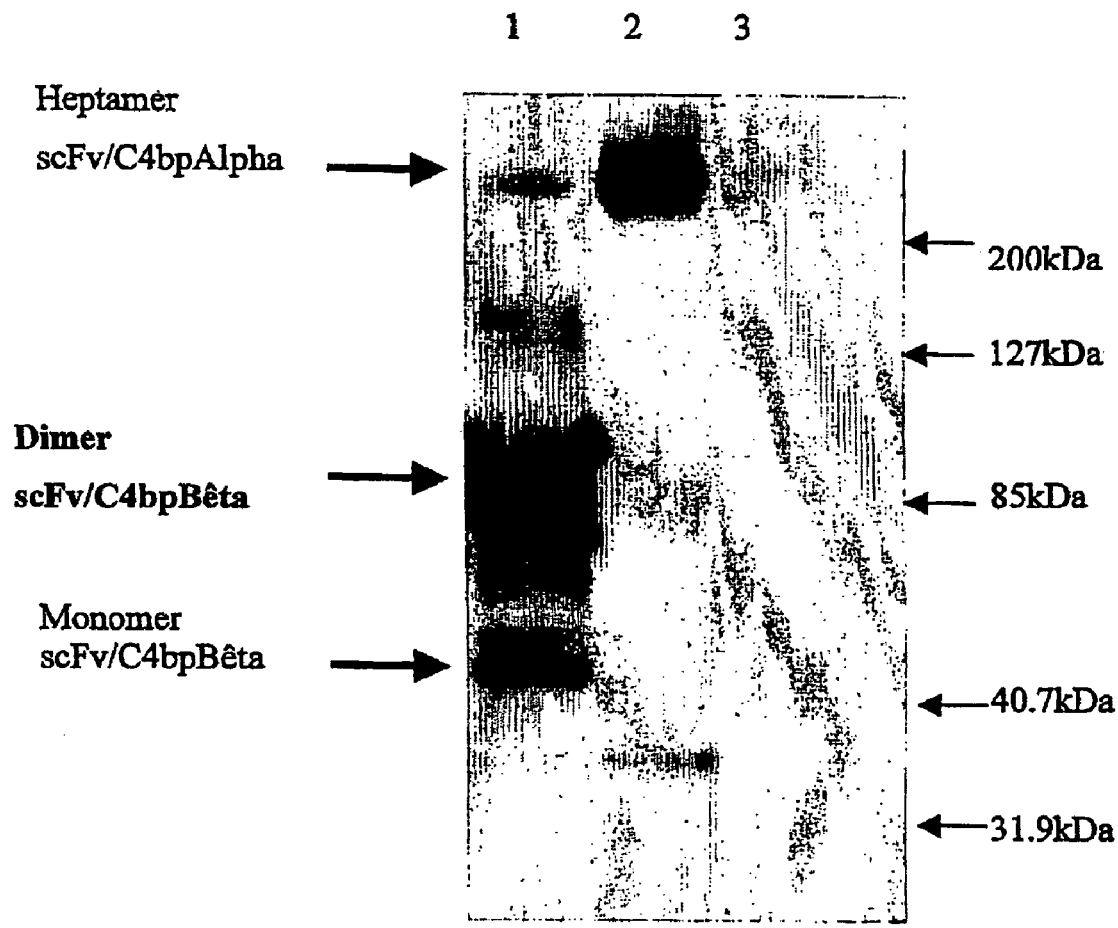
FIG. 2 is an autoradiogram of a Western Blot after revealing using a labeled anti-scFv antibody.
Figure 3:
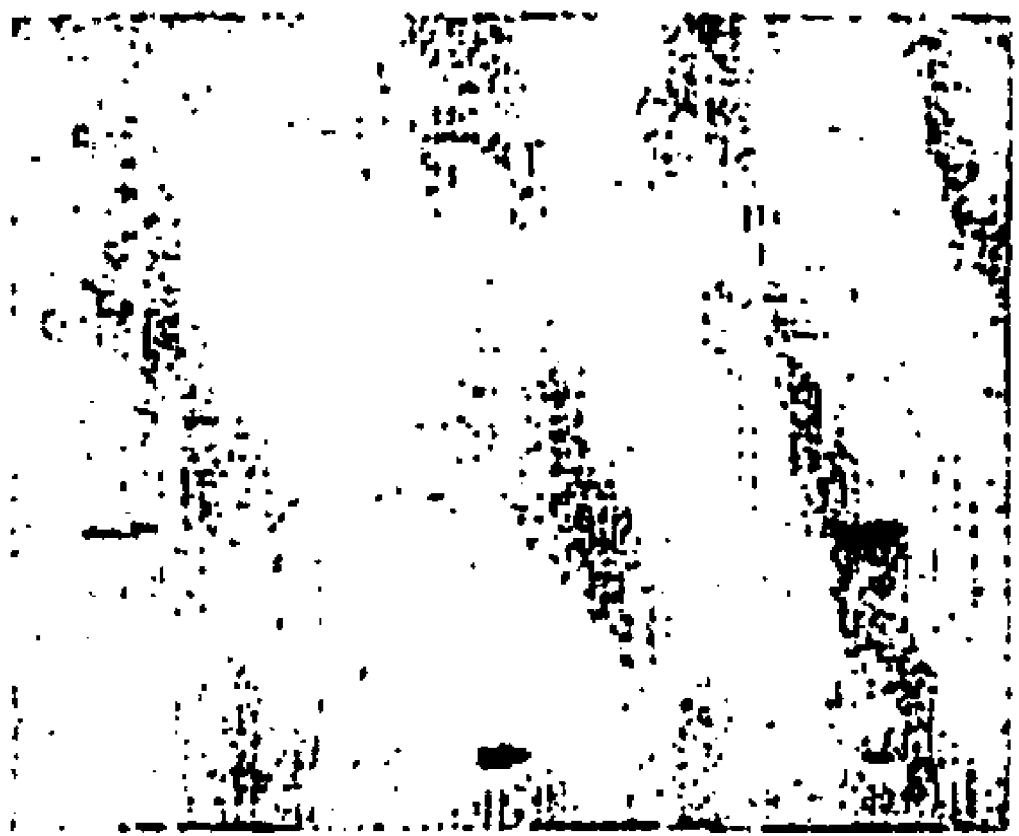
Figure 4:
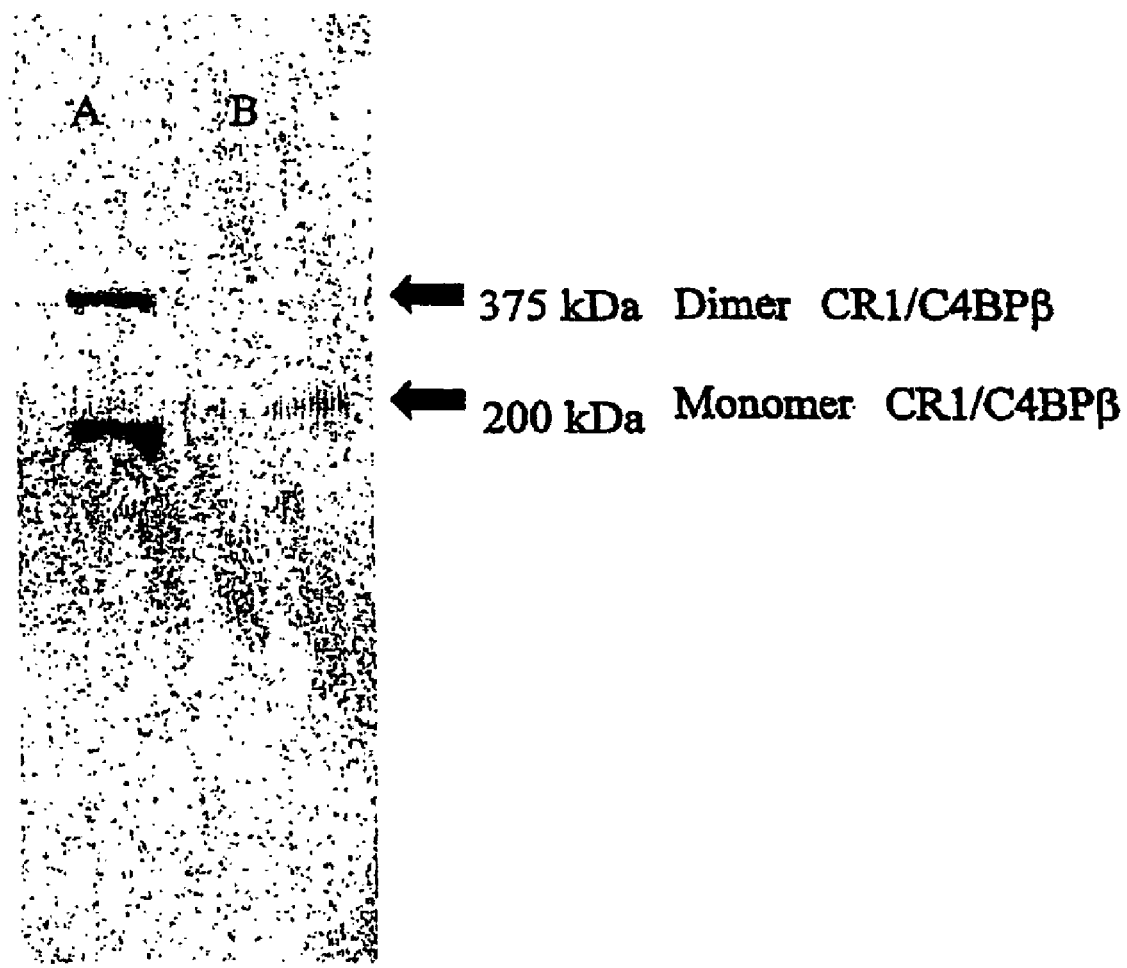

CHO cells transfected with a pKC3 expression vector (J Virol, 50, 1984, 606-614) expressing a CR1/C4BPβ fusion polypeptide were cultivated overnight in the presence of $^{32}$S methionine-cysteine. The culture supernatants were then immuno-precipitated by anti-CR1 J3D3 monoclonal antibody. The immunoprecipitated proteins then underwent PAGE-SDS electrophoresis (4% acrylamide) under non reducing conditions (track A) and reducing conditions (track B) (see FIG. 4). Two different proteins were immunoprecipitated, one with a molecular weight of 200 kDa (monomer) and the other with a molecular weight of 375 kDa (dimer). Once reduced, these two molecules had the same molecular weight.

These results confirm that the method of the invention produces proteins mainly in the form of dimers.

The invention claimed is:

1. A recombinant dimeric protein obtainable by the following method:
   a) transfecting host cells with a vector allowing expression of a nucleotide sequence coding for a fusion polypeptide, said fusion polypeptide comprising at least one fragment of the β chain of the human C4BP protein as defined in SEQ ID NO: 1, or a functional variant of said fragment being selected from the group consisting of:
      (a1) a functional variant whose sequence is modified with respect to SEQ ID NO: 1 by deletion of one or more amino acids not essential to the dimerization function and/or by conservative substitution of one or more amino acids essential to dimerization, provided less than 25% of the amino acids of SEQ ID NO: 1 have been deleted and/or substituted;
      (a2) a functional variant according to (a1), wherein the cysteines located at positions 10 and 24 of SEQ ID NO: 1, and the at least 3 amino acids upstream and downstream of each cysteine have been conserved;
      (a3) a functional variant whose sequence is modified with respect to SEQ ID NO: 1 by substitution of one of the cysteines located at positions 10 and 24 by a neutral amino acid chosen among the amino acids A, V, F, P, M, I, L and W, and at the same time, by substitution of another amino acid by a cysteine;
      (a4) a functional variant whose sequence is modified with respect to SEQ ID NO: 1 by insertion of a heterologous sequence of the β chain between the cysteines located at positions 10 and 24 of SEQ ID NO: 1; and
      (a5) a functional variant whose sequence is modified with respect to SEQ ID NO: 1 by deletion of amino acid residue(s) between the cysteines located at positions 10 and 24 of SEQ ID NO: 1;
      said fusion polypeptide further comprising a polypeptide which is heterologous to said β chain;
   b) culturing the transfected host cells under conditions which are suitable for expressing the nucleotide sequence coding for the fusion polypeptide and the covalent association of two fusion polypeptides in vivo to form a dimeric protein; and
   c) recovering the dimeric proteins formed.

2. A recombinant dimeric protein, which is constituted by two fusion polypeptides, each fusion polypeptide comprising at least a fragment of the β chain of the human C4BP protein as defined in SEQ ID NO: 1, or a functional variant of said fragment selected from the group consisting of:
   (a1) a functional variant whose sequence is modified with respect to SEQ ID NO: 1 by deletion of one or more amino acids not essential to the dimerization function and/or by conservative substitution of one or more amino acids essential to dimerization, provided less than 25% of the amino acids of SEQ ID NO: 1 have been deleted and/or substituted;
   (a2) a functional variant according to (a1), wherein the cysteines located at positions 10 and 24 of SEQ ID NO: 1, and the at least 3 amino acids upstream and downstream of each cysteine have been conserved;
   (a3) a functional variant whose sequence is modified with respect to SEQ ID NO: 1 by substitution of one of the cysteines located at positions 10 and 24 by a neutral amino acid chosen among the amino acids A, V, F, P, M, I, L and W, and at the same time, by substitution of another amino acid by a cysteine;

(a4) a functional variant whose sequence is modified with respect to SEQ ID NO: 1 by insertion of a heterologous sequence of the β chain between the cysteines located at positions 10 and 24 of SEQ ID NO: 1;

(a5) a functional variant whose sequence is modified from SEQ ID NO: 1 by deletion of amino acid residue(s) between the cysteines located at positions 10 and 24 of SEQ ID NO: 1;

said fusion polypeptide further comprising a polypeptide heterologous to said β chain.

3. A recombinant dimeric protein according to claim 2, wherein the fragment of the α chain of the human C4BP protein as defined in SEQ ID NO: 1, or the functional variant as defined in options (a1) to (a6), is fused to the C-terminal end of the heterologous polypeptide.

4. A dimeric protein according to claim 2, wherein the heterologous polypeptide is selected from the group constituted by enzymes, enzymatic activity regulating factors, receptor ligands, haptens, antigens, antibodies, antibody fragments, drugs and receptors, especially monochain receptors and proteic drug acceptors.

5. A dimeric protein according to claim 2, wherein the heterologous polypeptide is an antibody fragment comprising all or part of the variable regions of an antibody which is functional for antigen-antibody binding.

6. A recombinant heterodimeric protein, which is constituted by a first and a second fusion polypeptide, each fusion polypeptide comprising at least one fragment of the β chain of the human C4BP protein as defined in SEQ ID NO: 1, or a functional variant of said fragment selected from the group consisting of:

(a1) a functional variant whose sequence is modified with respect to SEQ ID NO: 1 by deletion of one or more amino acids not essential to the dimerization function and/or by conservative substitution of one or more amino acids essential to dimerization, provided less than 25% of the amino acids of SEQ ID NO: 1 have been deleted and/or substituted;

(a2) a functional variant according to (a1), wherein the cysteines located at positions 10 and 24 of SEQ ID NO: 1, and the at least 3 amino acids upstream and downstream of each cysteine have been conserved;

(a3) a functional variant whose sequence is modified with respect to SEQ ID NO: 1 by substitution of one of the cysteines located at positions 10 and 24 by a neutral amino acid chosen among the amino acids A, V, F, P, M, I, L and W, and at the same time, by substitution of another amino acid by a cysteine;

(a4) a functional variant whose sequence is modified with respect to SEQ ID NO: 1 by insertion of a heterologous sequence of the β chain between the cysteines located at positions 10 and 24 of SEQ ID NO: 1; and (a5) a functional variant whose sequence is modified with respect to SEQ ID NO: 1 by deletion of amino acid residue(s) between the cysteines located at positions 10 and 24 of SEQ ID NO: 1, said first fusion polypeptide further comprising a polypeptide heterologous to said β chain, and the second fusion polypeptide comprising a second polypeptide heterologous to said β chain which differs from the first heterologous polypeptide.

7. A recombinant heterodimeric protein according to claim 6, wherein the fragment of the β chain of the human C4BP protein as defined in SEQ ID NO: 1 of the first and second fusion polypeptide, or the functional variant as defined in options (a1) to (a6), are respectively fused to the C-terminal end of the first polypeptide and the second heterologous polypeptides.

8. A heterodimeric protein according to claim 6, wherein the first and second heterologous polypeptides are selected, independently of each other, from the group constituted by enzymes, enzymatic activity regulating factors, receptor ligands, haptens, antigens, antibodies, antibody fragments, drugs and receptors, especially monochain receptors and proteic drug acceptors.

9. A heterodimeric protein according to claim 8, wherein the antibody fragment comprises all or part of the variable regions of an antibody which is functional for antigen-antibody binding.

10. A heterodimeric protein according to claim 6, wherein the first and second heterologous polypeptides are different ligands.

11. A heterodimeric protein according to claim 6, wherein the first and second heterologous polypeptides are different antibody sites.

12. A heterodimeric protein according to claim 6, wherein the first and second heterologous polypeptides are different monochain receptors.

13. A heterodimeric protein according to claim 6, wherein the first heterologous polypeptide is an antibody and the second heterologous polypeptide is a drug.

14. A heterodimeric protein according to claim 6, wherein the first heterologous polypeptide is an antibody and the second heterologous polypeptide is a proteic drug acceptor.

15. A dimeric or heterodimeric protein according to claim 2, wherein said fusion polypeptides are associated by covalent bonding between two cysteines of the β chain fragment of the human C4BP protein.

* * * * *

SEQUENCE LISTING

<160> NUMBER OF SEQ ID NOS: 1

<210> SEQ ID NO 1
<211> LENGTH: 60
<212> TYPE: PRT
<213> ORGANISM: Homo sapiens

<400> SEQUENCE: 1

```
Leu Ile Gln Glu Ala Pro Lys Pro Glu Cys Glu Lys Ala Leu Leu Ala
1               5                   10                  15

Phe Gln Glu Ser Lys Asn Leu Cys Glu Ala Met Glu Asn Phe Met Gln
            20                  25                  30

Gln Leu Lys Glu Ser Gly Met Thr Met Glu Glu Leu Lys Tyr Ser Leu
        35                  40                  45

Glu Leu Lys Lys Ala Glu Leu Lys Ala Lys Leu Leu
    50                  55                  60
```